United States Patent [19]

Egger et al.

[11] Patent Number: Plant 7,329

[45] Date of Patent: Sep. 18, 1990

[54] GAZANIA PLANT CALLED 'MITSUWA BETTER WHITE'

[75] Inventors: Janet N. Egger, Ventura; Stephen H. Beimel, Agoura, both of Calif.

[73] Assignee: Mitsuwa Nursery, Inc., Moorpark, Calif.

[21] Appl. No.: 349,859

[22] Filed: May 10, 1989

[51] Int. Cl.[5] ..... A01H 5/00

[52] U.S. Cl. ..... Plt./68

[58] Field of Search ..... Plt./68

*Primary Examiner*—James R. Fevre

*Attorney, Agent, or Firm*—Roylance, Abrams, Berdo & Goodman

[57] ABSTRACT

A perennial hybrid Gazania groundcover which is distinguished by the clear white color of its flowers and its green trailing foliage. In addition, the invention plant is floriferous, vigorous, and disease and frost tolerant.

1 Drawing Sheet

BACKGROUND OF THE INVENTION

The present invention relates to a new and distinctive cultivar of Gazania plant botanically known as *Gazania rigens* hybrid and referred commercially by the cultivar name 'Mitsuwa Better White'. *Gazania rigens* 'Mitsuwa Better White' was discovered in the mother stock field of Mitsuwa Nursery in Moorpark, Calif. It originated as a natural hybrid. Its parents are unknown. The field contained *Gazania rigens* and *Gazania rigens* var. *leucoleana* and their cultivars.

BRIEF DESCRIPTION OF THE INVENTION

*Gazania rigens* 'Mitsuwa Better White' is a perennial trailing groundcover with excellent vigor, hardiness, green leaves, and numerous showy clear white flowers that bloom from February through December in Southern California. Its outstanding vigor, disease tolerance, and hardiness are believed to be a substantial step forward and an important advantage for *Gazania rigens* 'Mitsuwa Better White' as compared to all other white flowering Gazania groundcovers.

DESCRIPTION OF THE DRAWING

The accompanying color photograph, forming a part of this disclosure, was taken in Summer 1988 in a greenhouse in Moorpark, Calif., and shows a close-up of *Gazania rigens* 'Mitsuwa Better White' growing in a flat; the view being more or less straight down onto the plants. The photograph shows the typical flower and foliage form and color as true as is reasonably possible in this type of color photograph.

The primary distinguishing characteristics of *Gazania rigens* 'Mitsuwa Better White' are vigor, numerous clear white flowers, and green leaves. To the inventors' knowledge, there is only one other unbanded white flowering Gazania groundcover with green foliage and a trailing habit commercially available. This other white flowering Gazania groundcover is *Gazania rigens* 'Mitsuwa White'. *Gazania rigens* 'Mitsuwa White' is described and claimed in U.S. Plant Pat. No. 5,797 issued Nov. 4, 1986, and is commonly owned by Mitsuwa Nursery, Inc. with the present invention. In comparison to *Gazania rigens* 'Mitsuwa White', *Gazania rigens* 'Mitsuwa Better White' is more vigorous, lower growing, more free-flowering, hardier, and more disease tolerant. 'Mitsuwa Better White' has leaves which are smaller, thinner, narrower, and lighter green. The flowers of *Gazania rigens* 'Mitsuwa Better White' are the same size and color as those of *Gazania rigens* 'Mitsuwa White', but its petals are narrower and have a slight twist to them while mature. This gives the flowers of *Gazania rigens* 'Mitsuwa Better White' a starry appearance. *Gazania rigens* 'Mitsuwa Better White' has the same excellent flower size and plant spread as *Gazania rigens* 'Mitsuwa White'.

DETAILED DESCRIPTION

The following is a detailed description of *Gazania rigens* 'Mitsuwa Better White' based on such plants produced using normal commercial practices outdoors at Mitsuwa Nursery, Inc. in Moorpark, Calif. Color references are made to The Royal Horticultural Society Colour Chart except where the context indicates a term having its ordinary dictionary meaning.

Parentage: A natural outcross within the *Gazania rigens* and the *Gazania rigens:* var. *leucoleana* groups.

Plant form: Plants are a vigorous growing, trailing groundcover.

Habit of growth: Plants are decumbent, spreading rapidly to approximately 1 meter in diameter. Plants form a dense carpet to approximately 12 cm in height.

Foliage: Foliage is a medium green with simple alternate leaves.

(1) *Size.*—Mature leaves are approximately 8–11 cm in length and 1 cm in width at the widest point.

(2) *Shape.*—Oblanceolate. Occasionally a leaf is asymmetrically 3-pinnatifid.

(3) *Texture.*—The topside of the leaf is glabrous, the bottom side is tomentose.

(4) *Margin.*—Subrevolute.

(5) *Color.*—Young foliage: topside — 144 A; underside — 155 D. Mature foliage: topside — 137 C; underside — 155 D.

Flower description: The flowers are a clear unbanded white and the plants are very floriferous.

(1) *Habit.*—The flower heads arise from leaf axils on peduncles to approximately 15 cm in length.

(2) *Season of bloom.*—Varies with the climate. In Moorpark, Calif., heavy bloom occurs from approximately late February to early December.

(3) *Flower parts.*—(a) Flower heads measure 5 to 6½ cm acrosss. (b) Ray petals measure up to 4 cm in length and have a slight twist at the base when mature. Each ray petal is white in color except at the very base where it is bright yellow. The underside of each ray petal has a dark section down the center between the two main veins. This stripe begins at the tip and travels down three quarters of the petal.

(4) *Color.*—Disc flowers (closed) — 21 A; Ray flowers: topside: tip — 155 A; middle — 4 C; base — 13 A. Bottomside: tip edges — 4 D; dark section — 183 B.

Disease resistance: No disease problems noted.

Hardiness: *Gazania rigens* 'Mitsuwa Better White' has proven very frost tolerant. In winter of 1987, the Gazania trial fields in Moorpark, Calif. were frosted. Many of the Gazanias died and most died back. Almost all had leaf burn. *Gazania rigens* 'Mitsuwa Better White' showed no frost damage whatsoever.

Propagation: Asexual reproduction by stem cuttings has shown that the unique features of this new Gazania are stable and are reproduced true to type in successive propagations. *Gazania rigens* 'Mitsuwa Better White' roots rapidly under warm conditions.

We claim:

1. A new and distinct cultivar of Gazania are described and illustrated, particularly characterized by its floriferous showy clear white flowers, green foliage, vigorous growth, and trailing habit.

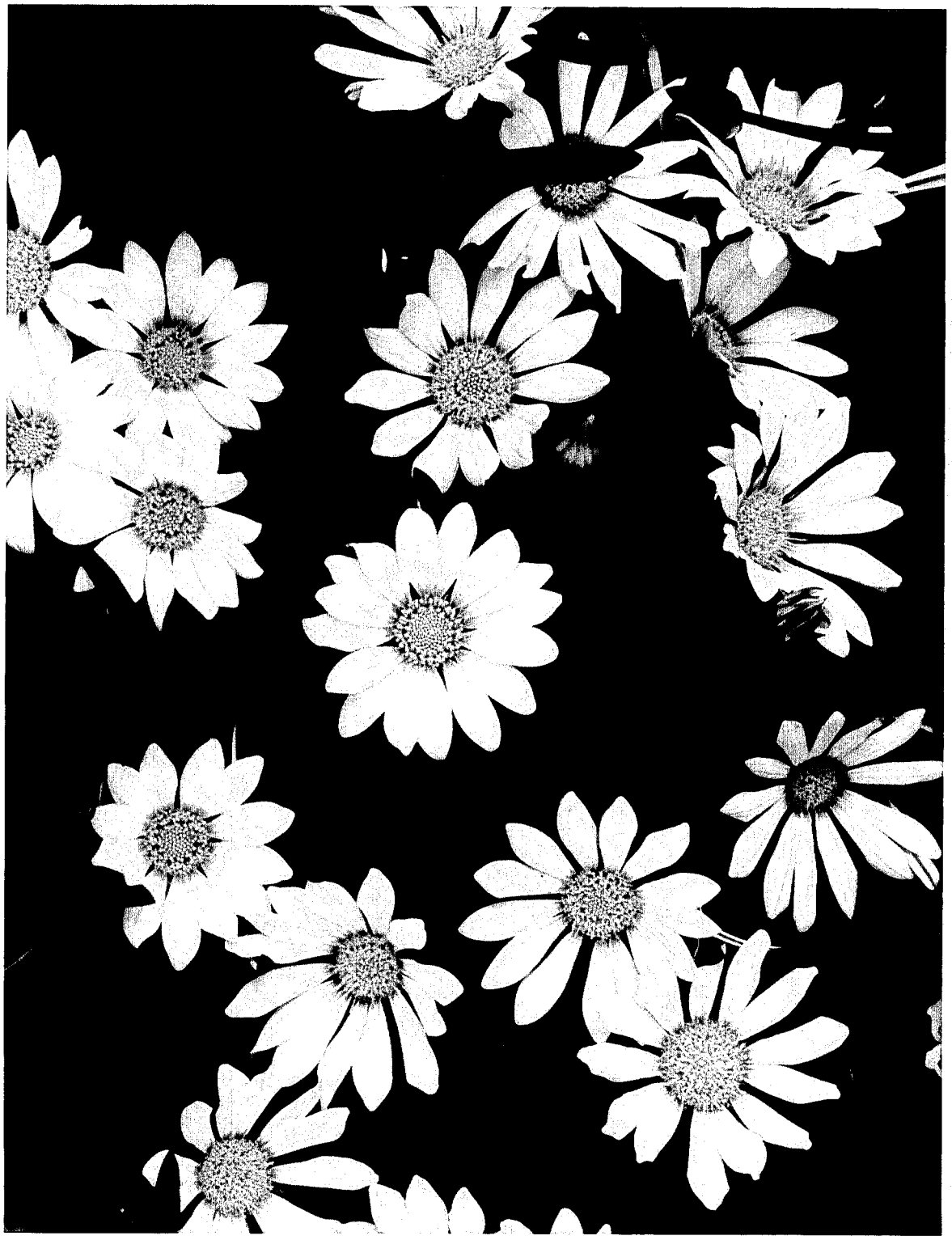

* * * * *